(12) United States Patent
Yura et al.

(10) Patent No.: US 7,005,513 B1
(45) Date of Patent: Feb. 28, 2006

(54) FUNCTIONALIZED GLYCOSAMINOGLYCAN POLYMER AND MEDICAL INSTRUMENTS AND DRUGS BY USING THE SAME

(75) Inventors: Hirofumi Yura, Kawasaki (JP); Yoshio Saito, Yokohama (JP); Masayuki Ishihara, Tachikawa (JP); Katsuaki Ono, Tokorozawa (JP); Keiichi Ishikawa, Tokorozawa (JP)

(73) Assignee: Netech, Inc., Kanagawa (JP)

( * ) Notice: Subject to any disclaimer, the term of this patent is extended or adjusted under 35 U.S.C. 154(b) by 0 days.

(21) Appl. No.: 09/937,991

(22) PCT Filed: Mar. 30, 2000

(86) PCT No.: PCT/JP00/02012

§ 371 (c)(1),
(2), (4) Date: Jan. 23, 2002

(87) PCT Pub. No.: WO00/59967

PCT Pub. Date: Oct. 12, 2000

(30) Foreign Application Priority Data

Apr. 2, 1999 (JP) .................................. 11/097062

(51) Int. Cl.
*C08B 37/00* (2006.01)
*C07H 7/00* (2006.01)

(52) U.S. Cl. ................. 536/55.1; 536/1.11; 536/4.1; 536/46; 536/51; 536/123.1; 514/54; 514/56; 514/59; 526/200; 526/238.23

(58) Field of Classification Search ........... 514/54, 514/56, 59; 536/1.11, 4.1, 46, 51, 55.1, 123.1; 526/200, 238.23
See application file for complete search history.

(56) References Cited

U.S. PATENT DOCUMENTS

| 4,415,490 A | * | 11/1983 | Joh .......................... 525/54.2 |
| 4,987,181 A | | 1/1991 | Bichon et al. |
| 5,250,519 A | * | 10/1993 | Conrad et al. ............... 514/56 |

FOREIGN PATENT DOCUMENTS

| JP | 8-85704 | | 4/1996 |
| JP | 10-324702 | | 12/1998 |
| WO | WO 91/15252 | * | 10/1991 |
| WO | WO 93/05793 | * | 4/1993 |
| WO | WO 94/01468 | | 1/1994 |

OTHER PUBLICATIONS

Tay, S. W. et al "Activity toward thrombin-antithrombin of heparin immobilized on two hydrogels", Biomaterials, 1989, vol. 10(1) pp 11-15.*
Nilsson et al, Biochemical and Biophysical Research Communications, 1981, 102(1), 449-457.*
Tay, s. W. et al, Biomaterials, 1989, 10, 11-15.*
American Heritage Dictionary of the English Language, Fourth Edition, 2000.*

* cited by examiner

*Primary Examiner*—James O. Wilson
*Assistant Examiner*—Ganapathy Krishnan
(74) *Attorney, Agent, or Firm*—Pearne & Gordon LLP

(57) ABSTRACT

The present invention provides a functionalized polymer which can be used extensively in the field of medical drugs as well as medical devices and which is obtainable in an organic synthetic manner from glycosaminoglycan controlling adhesion, migration and proliferation of cells via linkage to various cellular growth factors or cytokines or direct interactions with the cells. The functionalized polymer of the present invention is characterized in that it comprises a carbohydrate corresponding to at least a part of the basic structure of glycosaminoglycan introduced into a vinyl-type polymer chain.

9 Claims, 3 Drawing Sheets

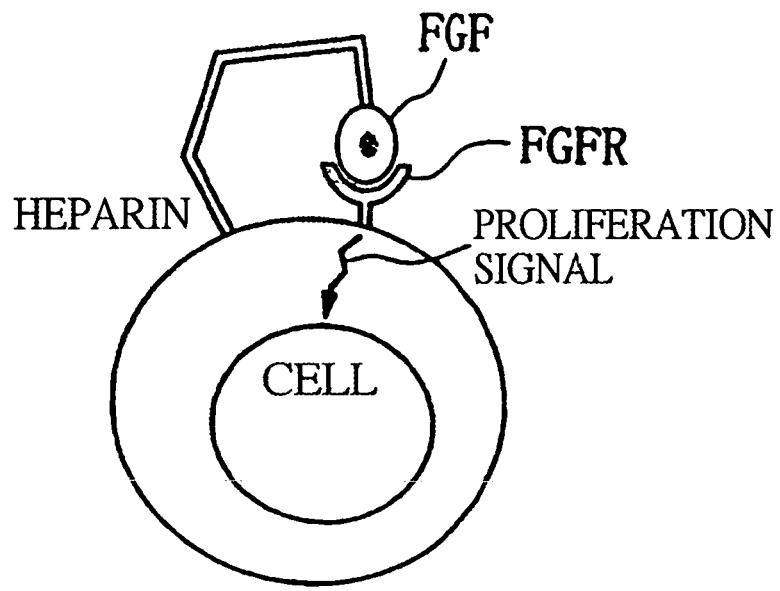
FIG. 1  MICHANISM OF CELL PROLIFERATION
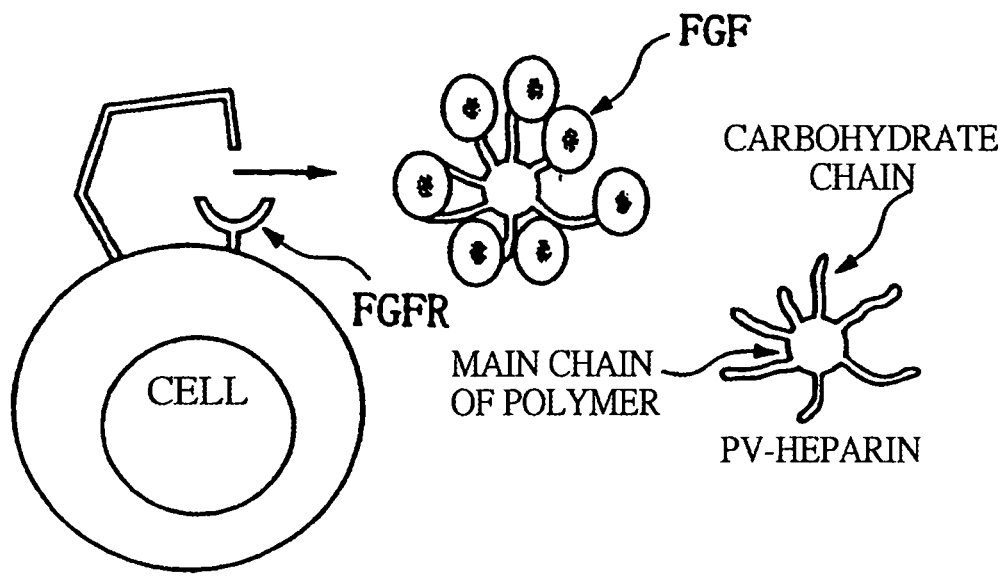
FIG. 2  FUNCTION MECHANISM OF ANTITUMOR ACTIVITY — P-I-14
--- Native Heparin
······ Periodic Acid Decomposed Low-Molecular-Weight Heparin

FUNCTIONALIZED GLYCOSAMINOGLYCAN POLYMER AND MEDICAL INSTRUMENTS AND DRUGS BY USING THE SAME

FIELD OF THE INVENTION

The present invention relates to a novel polymeric material formed by incorporating into a vinyl polymer the structure of glycosaminoglycans which are natural polysaccharides that bind with various cell growth factors and cytokines to control cell proliferation, and its application to medicine.

BACKGROUND ART

The acidic polysaccharide group known as glycosaminoglycans (GAG) including heparin/heparan sulfate (HS), chondroitin sulfate, dermatan sulfate, keratan sulfate and hyaluronic acid attach to core proteins by means of covalent bonds, forming proteoglycans (PG) which are present in connective tissue and cell membranes. PG's, along with other cell-adhesive proteins, form the extracellular matrix, and are widely distributed in order to enable cells to live and to perform biological functions. In particular, heparan sulfate proteoglycans (HS-PG) are present in the tissue of almost all animals, and perform the extremely important functions of cell adhesion, morphogenesis and maintenance of functions.

Additionally, it has become clear that heparin/HS contained in PG's interacts with various types of cell growth factors and plays a considerable role in the control of cell differentiation and proliferation. Fibroblast growth factors (FGF) form the FGF family (currently, FGF1–FGF10 are known) having a high affinity with heparin/HS, and act with specificity with respect to vascular endothelial cells, Kaposi's sarcoma cells and epidermal keratinocytes. Such activity of FGF's is believed to occur as a result of binding specifically to FGF receptors (FGFR) on the cell surface. That is, as shown schematically in FIG. 1, heparin/HS pierces the membrane holds and preserves unstable FGF molecules in a stable state in the vicinity of the cell, and supports FGF bonds to the receptors (FGFR) on the cells as needed while protecting the FGF from proteolytic enzymes and oxidative decomposition. The FGF bonding to the FGFR causes the proliferation signal to be transmitted and promotes cell proliferation. This mechanism has been proven by much research which suggests that FGF's and FGFR's cannot bind without the presence of heparin/HS (for example, see M. Ishihara, *Glycobiology,* 4, 817–824 (1994)).

Heparin/HS is composed of a repeating structure of disaccharides including uronic acid having a carboxymethyl group and glucosamin having an acetyl group, and an important characteristic is the sulfation of hydroxyl groups and amino groups present in the molecule in various proportions. About 10 types of sulfation of the disaccharides have been identified, and heparin and HS are divided depending on differences in the sulfation. Additionally, cells are believed to control the activity of the FGF family by themselves preparing various types of heparin/HS of different levels of sulfation and molecular chain lengths according to their type and state.

Aside from controlling the activity of FGF, heparin/HS, which can take various sulfate structures as described above, interact with roughly 80% of cytokines which contribute to a wide range of biological reactions from cellular migration and proliferation to inflammatory reaction, with matrix adhesion molecules, metabolism-related substances and blood coagulation factors, thus performing an extreme variety of functions in the body. However, due to this multifunctionality, heparin/HS can oftentimes cause unwanted side effects when the native heparin/HS molecule is entirely used, thus restricting the use of heparin/HS in the field of pharmaceuticals and medicine.

On the other hand, the various functions of heparin/HS are known to change dramatically according to the molecular chain length. For example, while antithrombin III which inhibits blood coagulation binds with a characteristic structural domain having a 3-O-sulfate group contained in heparin/HS, a sequence of at least 5 saccharides is necessary to express this anti-coagulant activity, so that in actual practice, smaller molecules make reduced activity inevitable. Additionally, in order to ensure expression of FGF1 and FGF4 activity, a structural domain of at least 10 saccharides containing an abundance of 2-O-sulfate groups and 6-O-sulfate groups is necessary.

Recently, experiments have been performed to use the active domain of heparin/HS molecules as oxidatively fragmented heparinoids for the purpose of controlling only the cell growth factor activity among the various complexed functions of heparin/HS (M. Ishihara et al., *J. Biol. Chem.,* 268, 4675–4683 (1993)). However, this research brought to light such problems as the control for the activity of various types of growth factors due to the heparinoid fragments being inadequate, and side effects such as higher bleeding tendencies due to increasing the concentration of heparinoids needed in order to maintain the desired activity.

Furthermore, in order to apply GAGs containing heparin/HS to various fields, they must be efficiently attached to hydrophobic resin products commonly used in the medical field such as polystyrenes and polycarbonates, but GAGs and their fragments generally have a high water solubility and are difficult to adsorb and attach firmly to the various resin products so that, for example, it is difficult to apply GAGs to diagnostic beads or culture dishes in order to make them useful for general basic medical research or clinical medicine.

SUMMARY OF THE INVENTION

As a result of repeatedly performing diligent research to solve the above-described problems, the present inventors discovered that by means of a functionalized polymer characterized by incorporating a carbohydrate chain containing a structure corresponding to at least a portion of a basic glycosaminoglycan skeletal structure into a vinyl polymer main chain, it is possible to adequately activate desired activity without side effects, and especially to enable the adhesion and fixation to hydrophobic resin products used in the medical field with ease and at a high density.

The structure of the functionalized polymer of the present invention takes a vinyl polymer as the main chain, and incorporates a carbohydrate chain containing a structure corresponding to at least a portion of the basic skeletal structure of a glycosaminoglycan (GAG) on this main chain. That is, the functionalized polymer of the present invention includes at least one, preferably a plurality of active GAG domains in a single molecule, whereby the interaction of biological activity of these active domains, particularly in the case of heparin/HS, is more greatly reinforced with respect to various cell growth factors and cytokines.

Additionally, the present invention also offers a medical instrument with the surface modified by means of such functionalized polymers. Since these types of medical instruments have GAGs affixed to the surface, they are useful, for example, for cell culture and diagnosis equipment.

Furthermore, the functionalized polymers of the present invention also offer a drug based on the cell growth inhibiting effect of GAGs, particularly a cell growth controlling agent, more specifically including anti-tumor agents.

BRIEF DESCRIPTION OF THE DRAWINGS

FIG. 1 is a schematic diagram for explaining the mechanism of cell proliferation.

FIG. 2 is a schematic diagram showing an example of the functional mechanism of an anti-tumor agent of the present invention.

PREFERRED MODE FOR CARRYING OUT THE INVENTION

Figure 3:
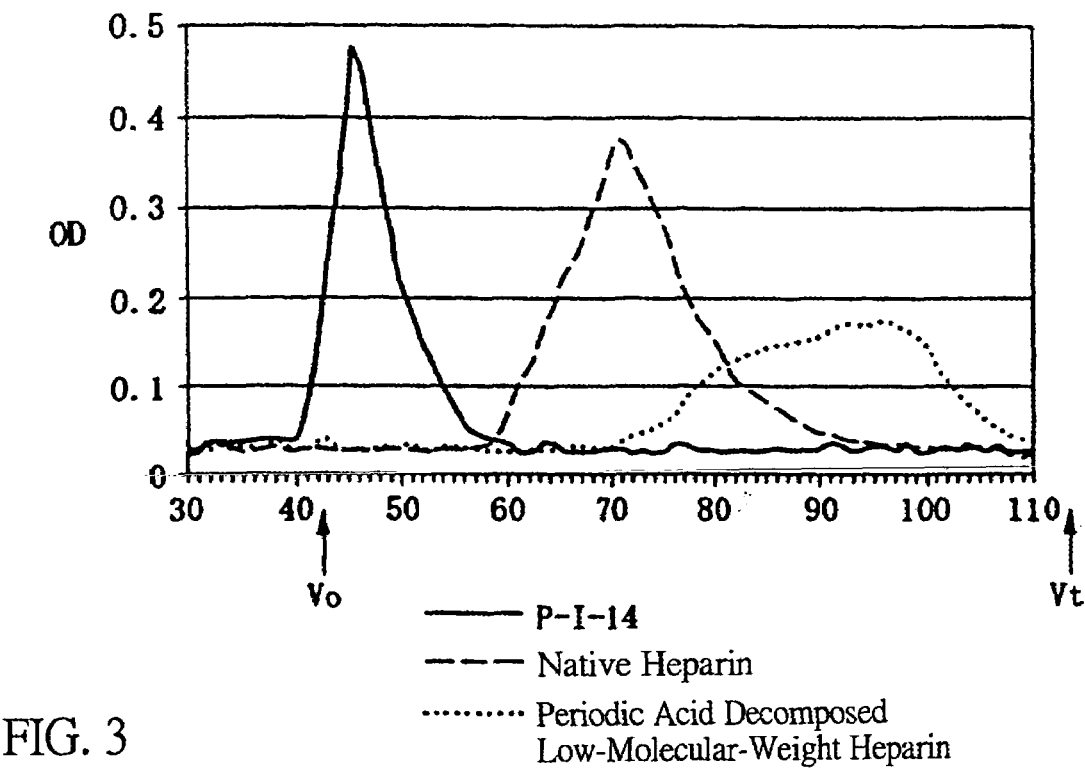
FIG. 3 is a graph showing a gel filtration pattern for Example 1.

Herebelow, the functionalized polymers of the present invention shall be described in further detail.

The vinyl polymer used as the main chain in the functionalized polymer of the present invention may be any homopolymer or copolymer composed of a polymerizable monomer, which can for example be selected arbitrarily from the addition polymerization type, condensation polymerization type, polyaddition type, addition condensation type and open circular type monomers described in the *Chemical Handbook* (Applied Chemistry Edition 1, Chemical Society of Japan, Maruzen, 1987), and is not particularly restricted. Preferably; it should be a polymer of an addition polymerizable monomer having at least one unsaturated bond, such as ethylene, propylene, styrene, vinyl acetate, acrylic acid or acrylamide, and these can be arbitrarily substituted.

A carbohydrate chain containing a structure corresponding to at least one portion of a basic glycosaminoglycan skeletal structure is bonded to this main polymer chain. That is, the functionalized polymer of the present invention contains at least one unit expressed by the following general formula (1).

(1)

In the above formula, W denotes a carbohydrate chain, X, Y and Z denote arbitrary substituent groups containing hydrogen atoms, and n denotes the number of repeating units of at least 1.

The carbohydrate chain composing the functionalized polymer of the present invention has a structure corresponding to at least a portion of the basic skeletal structure forming GAGs such as heparin/HS, chondroitin sulfate, dermatan sulfate and keratan sulfate, the number of constituent disaccharide units being at least 2–50, more preferably being 4–25 oligosaccharides or polysaccharides, each constituent disaccharide unit having an average of at least one sulfate group. For example, a carbohydrate chain composed of a sequence of at least 5 saccharides corresponding to a characteristic structural domain having a 3-O-sulfate group contained in the heparin/HS binds specifically to antithrombin III which inhibits blood coagulation, and a carbohydrate chain corresponding to a structural domain of a sequence of at least 10 saccharides containing 2-O-sulfate groups and 6-O-sulfate groups in abundance contributes to the expression of FGF1 and FGF4 activity.

The above-described carbohydrate chain may be modified by selective desulfation of N-sulfate groups or chemically synthesized, or may be natural. However, it is structurally preferable to use decomposed carbohydrate chains obtained by chemical decomposition of natural glycosaminoglycans, these decomposed carbohydrate chains binding to the main polymer chain via functional groups formed by the chemical decomposition.

Examples of these natural glycosaminoglycans include GAGs such as heparin/HS, chondroitin sulfate, dermatan sulfate, and keratan sulfate, of which heparin/HS which has many sulfation patterns for its constituent saccharides are more preferable, but there is no problem in using other types of GAGs. Additionally, it is possible to use homopolysaccharides such as cellulose, amylose, laminaran, agarose, carrageenan, inulin, levan, xylan, mannan, chitin, pectin, amylopectin, galactan, tritisin, arabinan and colominic acid, heteropolysaccharides such as glucomannoglycan, galactoglucomannoglycan, guar gum, arabinogalactoglycan, gum arabic, traganthic acid and alginic acid, incorporating sulfate groups by enzymes or chemical synthesis.

The chemical decomposition of the natural glycosaminoglycans described above can be performed favorably by severing the carbohydrate chain bonds in the above-described polysaccharides using nitrous acid or periodic acid under non-physiological conditions outside the range of pH 6.5–8.0, preferably the acidic and/or alkaline regions of less than pH 5 or more than pH 10, thereby obtaining a fractionated carbohydrate chain. Additionally, it is also possible to use fractionated carbohydrate chains such as those obtained by enzymatic decomposition with enzymes which selectively decompose carbohydrate chains such as heparinase, heparitinase, chondroitinase and keratanase, or those decomposed by heat, plasma discharge, or those chemically decomposed by radical reactive reagents.

The carbohydrate chain in the functionalized polymer of the present invention binds to the polymer main chain by means of covalent bonds. The nature of these bonds is not particularly restricted, and they can be made by coupling together their functional groups using any catalyst under suitable reaction conditions according to the combinations of functional groups possessed by the polymer main chain and carbohydrate chain. Additionally, while it is possible to form a carbohydrate chain-derived monomer by binding a monomer constituting the polymer main chain with a carbohydrate chain, the carbohydrate chain-derived monomer should preferably be polymerized so as to be able to adjust the carbohydrate content in a single molecule. Among these, a functionalized polymer obtained by incorporating a fractionated hydrophilic carbohydrate chain into a hydrophobic monomer unit and polymerizing the resultant monomer has a property of water-soluble polymer due to its high density of carbohydrate chains in a single molecule and at the same time is capable of readily adhering to hydrophobic resin products.

The incorporation of carbohydrate chains in the functionalized polymer of the present invention can be performed, for example, by a Schiff bonding of aldehyde groups or carbonyl groups formed on chemically decomposed GAGs with amino groups of the monomers constituting the polymer. Furthermore, coupling agents having acid chloride groups, N-hydroxysuccinic acid imide ester groups or epoxy groups are suitable for use as methods for binding vinyl monomers with the functional groups of the carbohydrate chains. In particular, a method of using aldehyde groups formed on the GAGs by means of chemical decomposition is more preferably used due to its convenience and ability to preserve the activity of the GAGs.

Thus, the present invention offers a GAG-derived functionalized polymer having a plurality of active domains of natural GAGs in a single molecule, thereby reinforcing the biological activity of these active domains, in particular in connection with the interaction with various cell growth factors and cytokines in the case of heparin/HS.

Accordingly, the functionalized polymer of the present invention, due to its hydrophobisity of the polymer main chain, adheres to the surface of hydrophobic resins such as polystyrenes, polycarbonates, polyamides, polysulfones and polyesters used in synthetic resin products that are commonly used in medical applications to thereby modify the surface, enabling the tissue compatibility and blood compatibility of the surfaces of these products to be improved. Additionally, it can be coated onto microparticles or culture dishes and analysis plates composed of these resin products, thus enabling quantitative analysis of cell growth factors or efficient cell cultures using these carbohydrate chains.

Thus, the present invention also offers medical instruments with surfaces of hydrophobic resins such as polystyrenes or polycarbonates modified by the above-described functionalized polymers. These types of medical instruments can be readily manufactured by applying an aqueous solution of the functionalized polymer of the present invention onto the surfaces of instruments such as dishes, plates and beads, then drying, as a result of which GAGs are adsorbed and affixed to the surfaces at a high density. For example, by coating resin microbeads with the functionalized polymer of the present invention, various types of cell growth factors can be efficiently bound, thus giving a diagnostic tool for screening for disorders in which they play a role, and by coating a resin culture dish, it forms a culture system with cell growth effectively controlled, thus allowing for a wide range of applications in basic medicine and various clinical fields.

Additionally, since chondroitin sulfate and dermatan sulfate include cell adhesion control functions in their structures themselves, they are effective as surface treating agents for vessels or stents for preventing restenosis after Percutaneous Transluminal Coronary Angioplasty (PTCA).

Furthermore, the functionalized polymers of the present invention can firmly bind to various cell growth factors which are in a free state, so as to selectively absorb cell growth factors, cytokines, vascular growth factors and FGFs which contribute to the proliferation of cancer cells in tumor tissue, thereby to inhibit the growth of cancer cells or vascular endothelial cells and suppress the growth of tumors. Hence, the present invention also offers a cell growth control agent composed of the above-described functionalized polymer, particularly an anti-tumor agent (carcinostatic). For example, in hematic cancers such as acute lymphocytic leukemia or the like, some of the increased cancer cells are known to break off, create obstacles to blood flow and cause renal failure, and in such situations, heparin or the like is dripped intravenously to preserve the blood flow. At this time, a temporary reduction in blastogenesis of cancer cells is often observed, and this effect is believed to be due to the proliferation controlling function of heparin. That is, the anti-tumor agent of the present invention which has a plurality of heparin-like active domains is clearly effective not only for solid cancers but also for the treatment of hematic cancers such as leukemia.

Specifically, since the functionalized polymer of the present invention has a plurality of hydrophilic (water-soluble) carbohydrate chains bound to a hydrophobic polymer main chain, it is believed to exist in an aqueous solution with the polymer chain as a core, with the carbohydrate chains spread out in the vicinity thereof (FIG. 2, polyvinyl heparin (PV-heparin)). Therefore, a functionalized polymer having this type of structure (anti-tumor agent) is thought to be able to capture and absorb FGFs present around the cells so as to inhibit their binding to receptors as shown schematically in FIG. 2. Consequently, the anti-tumor agent of the present invention is believed to be based not on toxicity with respect to the cells, but follows a new functional mechanism by mainly inhibiting the new generation of blood vessels by oncocytes by absorbing vascular growth factors, thereby inhibiting the growth of the oncocytes, and is expected to be capable of being used as a safe anti-tumor agent which does not exhibit side effects that conventional anti-tumor agents possess.

EXAMPLES

Herebelow, the present invention shall be described in further detail by means of examples.

Example 1

Synthesis of Polyvinyl Heparins 25 g of sodium heparin (Scientific Protein Laboratories, USA) were dissolved in 400 ml of an acetate buffer solution (0.1 M, pH5) containing periodic acid, then stirred for a few days at 5° C. or less. To this, 20 ml of glycerol were added, and after stirring for an additional few hours, the reaction solution was put under dialysis for 2 days for desalination. After recovering the reaction solution and adding sodium hydroxide to adjust to a pH of 7.5, 21 g of a reaction product was obtained. 10 g of this was separated out and formed into an aqueous solution adjusted to a pH of 12 by means of sodium hydroxide, which was then stirred for a few hours at room temperature. After performing a dialysis operation similar to that described above on the reaction solution, the low-molecular-weight heparins were fractioned out using a gel filtration column (Bio-Gel, Bio-Rad), and the carbazole assay of Bitter et al. (T. Bitter and H. A. Muir, *Anal. Biochem.*, 4, 330–334 (1962)) was used to obtain a periodic acid-decomposed heparin having 20 saccharides in a center of molecular weight distribution (hereinafter referred to as I-20).

1 g of the native sodium heparin was dissolved in water and adjusted it pH to not more than 2 with 1 N hydrochloric acid. 20 mg of sodium nitrite was added to the prepared heparin solution and allowed to react for 2 hours. After dialysis for 2 days, low-molecular-weight heparin was fractionated using a gel filtration column (Bio-Gel, Bio-Rad). The fractionated carbohydrate chains were quantitated by the above-described carbazole method to obtain nitrite decomposed heparins having 6, 8, 10, and 12 saccharides (hereinbelow, termed as N-6, N-8, N-10, and N-12, respectively).

A vinylbenzylamine was synthesized in accordance with the method of Kobayashi et al. (K. Kobayashi et al., *Plym. J.*, 17, 567–575 (1985)). 300 mg each of the resulting I-20, N-6, N-8, N-10 and N-12 were dissolved in respectively 10 ml of a tetraethylmethylene diamine buffer solution (TEMED, pH 5), and 300 mg of vinylbenzylamine were added to each TEMED solution. 30 mg of a sodium cyanoborohydride aqueous solution were added to the solution formulated in this way, and this was stirred for 24 hours at room temperature. The reaction solution was desalinated by means of dialysis, and after filtering out the undissolved part, the result was freeze-dried to obtain a carbohydrate chain (I-20, N-6, N-8, N-10 and N-12) derived vinyl monomer.

The resulting carbohydrate chain-derived vinyl monomer was dissolved in 3 ml of water, and 4 mg of potassium peroxodisulfate were added. After deaeration and nitrogen replacement, this was sealed and allowed to react overnight at 63° C. The reaction solution was dripped into methanol to precipitate the product, after which the precipitate was filtered and recovered. The recovered substance was redissolved in water and a dialysis was performed, the unreacted part was removed by ultrafiltration (YM10, fractionation molecular weight 10,000, Amicon), and freeze-dried to purify to obtain polyvinyl heparin (PV-heparin). These PV-heparins shall be referred to as P-I-20, P-N-6, P-N-8, P-N-10 and P-N-12.

Example 2

Synthesis of Polyvinylated N-Desulfated Heparin 10 g of heparin (pyridinium salts) were dissolved in a mixed solution of 20 ml of distilled water and 380 ml of dimethylsulfoxide (DMSO), and this was stirred for 90 minutes at 50° C. to react. 1 g of the heparin, which had been obtained by dialysis followed by lyophilization and were N-desulfated but preserving the O-sulfate, was dissolved in 30 ml of a sodium carbonate solution (50 mM) containing 10 wt % of methanol, and after adding 1 ml of acetic anhydride on ice, the pH was adjusted to 7–8 using sodium hydroxide. This operation was repeated 5 times at intervals of 30 minutes to form N-acetylated heparin, which was put under dialysis and freeze-dried. This reaction product was polymerized based on acidification by periodic acid according to Example 1, thereby obtaining P-I-DSA 20 with an average of 20 saccharide chains.

Example 3

Synthesis of Polyvinylated Chondroitin Sulfate 0.5 g of chondroitin sulfate C (Seikagaku Kogyo, derived from shark cartilage) were dissolved in 5 ml of a hydrazine monohydrate containing 50 mg of hydrazinium sulfate, and this was allowed to react for 3.5 hours at 95° C. The partially hydrazine-decomposed product was put under dialysis for 1 day with flowing water, then freeze-dried, and the impurities removed by oxidation with a suitable amount of iodate. After putting under dialysis with flowing water for another 2 days and freeze-drying, the product was decomposed by nitrous acid in accordance with Example 1, to obtain P-N-20C with 20 saccharide chains.

Example 4

Synthesis of Polyvinylated Dermatan Sulfate

P-N-20D having 20 saccharide chains decomposed by nitrous acid was obtained in accordance with Example 3, with the exception of the fact that 0.5 g of chondroitin sulfate C were replaced by dermatan sulfate.

The synthesis reaction of a PV-heparin monomer derived from a low-molecular-weight heparin was confirmed by a vinyl group-originating peak in $^1$HNMR, and polymerization by homopolymerization of monomers was confirmed by broadening the peak of the $^1$HNMR and molecular weight fractionation due to gel filtration. For example, a gel filtration of P-I-20, native haparin and acid decomposed I-20 using Bio-Gel P-100 (Bio-Rad) provided a fractionation in order of uniform polymerized P-I-20, native heparin and periodic acid-decomposed I-20. This type of gel filtration pattern was able to be confirmed for polyvinylated GAGs of all types (see FIG. 3).

Example 5

Adsorption onto Resin Products

Aqueous solution containing a predetermined concentration of P-I-20 or native heparin was added to a polystyrene 96-well multiplate (Sumitomo Bakelite), and the carbohydrate concentration adhered to the polystyrene surface was evaluated after 24 hours using the above-mentioned carbazole method. The results are shown in FIG. 4.

Figure 4:
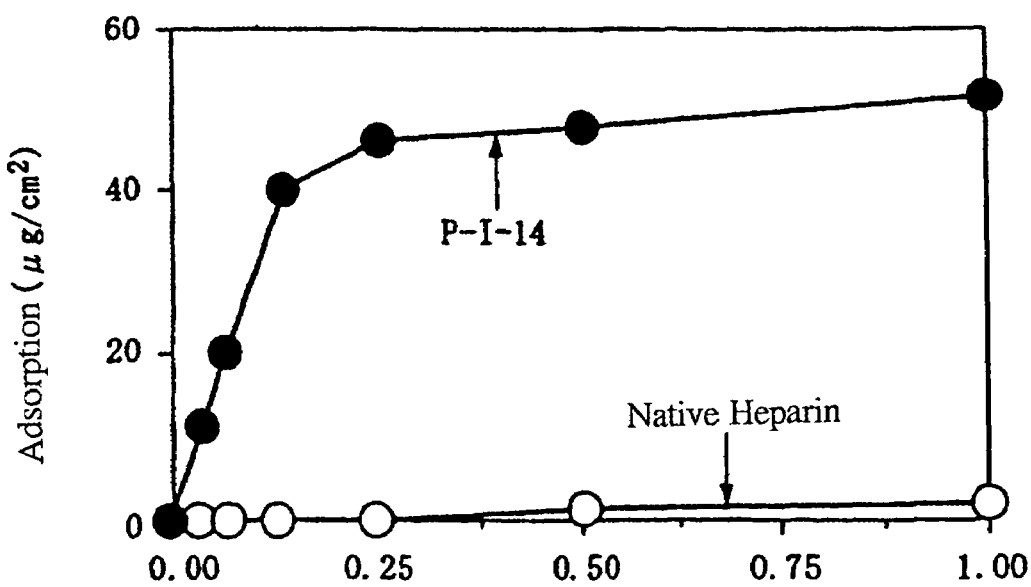
FIG. 4 is a graph showing the adsorption of functionalized polymers of the present invention for Example 2.

As shown in FIG. 4, the polyvinylated heparin (P-I-20) of the present invention adhered efficiently to the polystyrene surface, while native heparin did not adhere to the resin surface. In addition, the other polyvinylated heparins, such as P-N-12, P-N-10, P-N-8, and P-N-6 were observed adhesion amounts of 20–80 μg/ml at an addition concentration of 0.5 mg/ml. Furthermore, almost the same adhesion profiles were observed for polyvinylated N-desulfated heparin, polyvinylated chondroitin sulfate, and polyvinylated dermatan sulfate.

Furthermore, aside from polystyrene, similar adsorptive properties were observed in polycarbonates, polysulfones and polyurethanes. This indicates that the polyvinylated heparins of the present invention are an effective means of adsorbing and affixing heparin molecules to resin products for medical use. The functionalized polymers of the present invention also exhibited such efficient adsorption with respect to glass materials.

Example 6

Binding of Cell Growth Factor to Polyvinylated Heparin Coated Plate

100 μl of a phosphoric buffer solution (supplemented with 0.1% fetal bovine serum, pH 7.2) into which was dissolved a cell growth factor (FGF-2, HGF, VEGF 165) was added to a polystyrene 96-well multiplate (Sumitomo Bakelite) coated with the P-I-20 prepared in Example 1, and the binding ability of each cell growth factor was compared with untreated multiwells not coated with P-I-20.

An antibody against each growth factor (anti-FGF-2, anti-HGF, anti-VEGF (R&D System)) was made to react with the growth factor binding to the multiwell, and the antibodies after the reaction were further made to react with antibodies labeled with peroxidases, after which horseradish peroxidase substrate (Bio-Rad) was added to color. The amount of each growth factor that was bound was estimated from the OD value at 414 nm. The change in OD Values is shown in FIGS. 5(1), (2) and (3).

Figure 5:
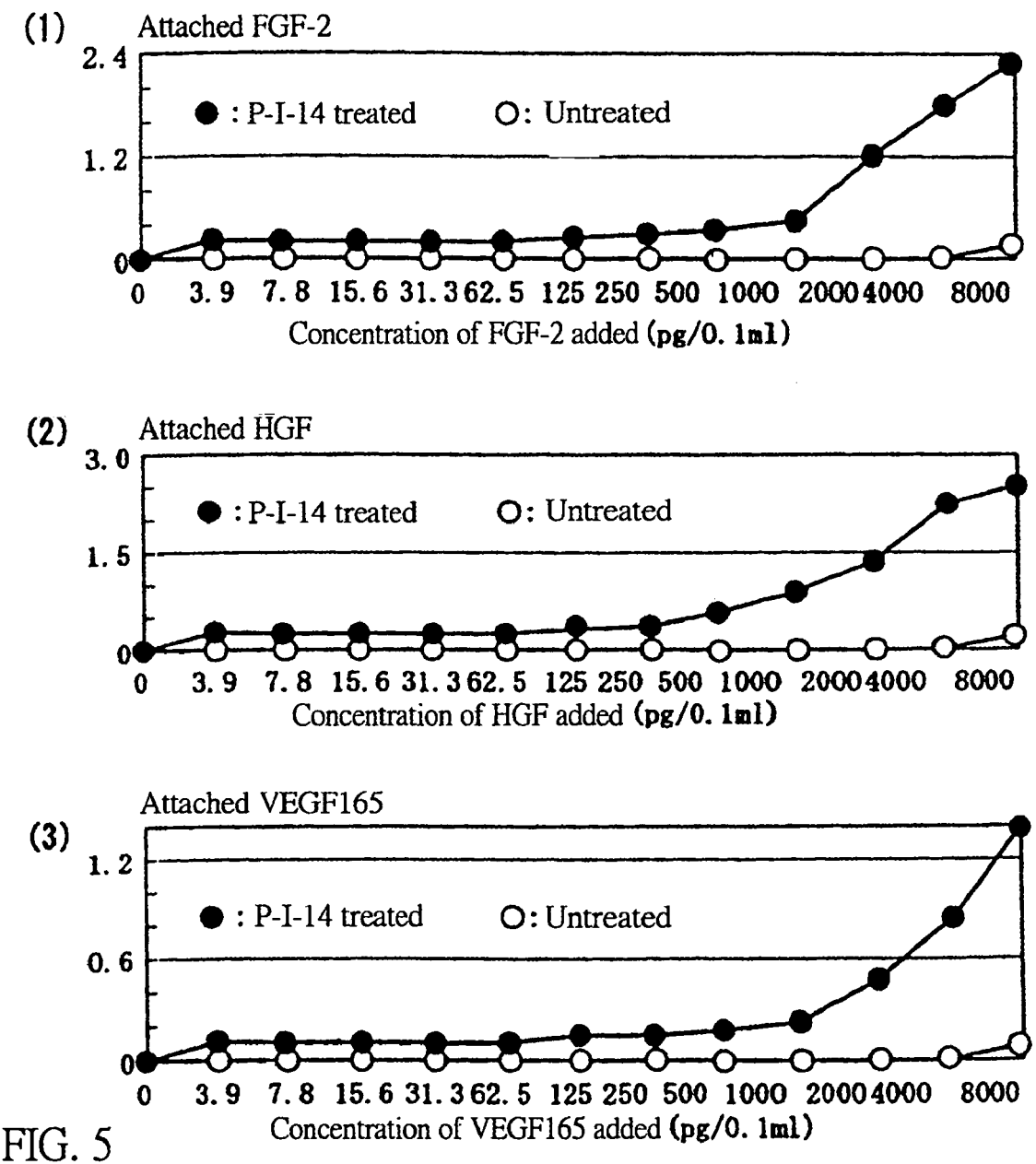
FIG. 5 is a graph showing the adhesion of cell growth factor through the functionalized polymers of the present invention for Example 3.

As shown in FIGS. 5(1), (2) and (3), in the dishes treated with the P-I-20 of the present invention, the added concentration of cell growth factor was confirmed to be at least 500 pg/0.1 ml, and coloration of the peroxidase based on binding of each growth factor was confirmed, but bonds were not observed in the untreated dishes. This indicates that the polyvinylated heparins of the present invention can specifically bind to various growth factors, and that the coloration based on the bonds of these growth factors was inhibited competitively by the addition of natural heparins. The above-given results indicate that the plates treated with the polyvinylated heparins of the present invention are able to detect cell growth factors and cytokines that increase with damage such as cancers or wounds easily and with high precision.

On the other hand, this type of characteristic growth factor binding activity was weak with polyvinylated N-desulfated heparin, polyvinylated chondroitin sulfates and polyvinylated dermatan sulfates.

Example 7

Cell Cultures on PV-Heparin Coated Tissue

A polystyrene 96-well multiplate was coated with aqueous P-I-20 or P-N-12 solutions (0.5 mg/ml) of the present invention, and also 2% gelatin and 10 µg/ml of human fibronectin solution, these were inoculated with 6,000 human coronary artery endothelial cells (CEC) suspended in a Dulbecco modified Eagle medium (10% fetal bovine serum added), after which FGF2 or VEGF165 were added as cell growth factors, and this was cultured from 3 days. After culturing, a WST-1 reagent (cell counting kit, Dojindo) was used to count the number of increased cells, and the results of an evaluation of the proliferation rate are shown in Table 1.

TABLE 1

| | CEC Proliferation Rate | | | |
|---|---|---|---|---|
| | Growth Factor | | | |
| | FGF2 | | VEGF165 | |
| Coating | 4 µg/l | 8 µg/l | 4 µg/l | 8 µg/l |
| None | 229 | 286 | 190 | 195 |
| P-I-20 | 392 | 408 | 364 | 404 |
| P-N-12 | 409 | 426 | 360 | 414 |
| Gelatin | 356 | 389 | 335 | 385 |
| Fibronectin | 273 | 327 | 371 | 436 |

As shown in Table 1, the rate of proliferation of vascular endothelial cells with respect to growth factors in the polyvinylated heparins of the present invention is clearly at least the same as fibronectin which is a cell adhesive protein. This suggests that the polyvinylated heparins allowed the cell growth factors to be increased and stabilized on the mutiplate surface, thereby maintaining good cell proliferation.

Example 8

Inhibition of Cell Growth Factor by Polyvinylated Heparins

The cell growth factor-dependent CECs of Example 7 were suspended in a culture medium with FGF2 or VEGF15 added at a concentration of 5 ng/ml, and these were cultured in a 96-well multiplate (Sumitomo Bakelite) for cell cultures. Additionally, P-I-20 and P-N-12 which are polyvinylated heparins of the present invention, native heparins, periodic acid oxidated I-20 and nitrous acid decomposed N-12 were simultaneously added at a concentration of 0 to 512 µg/ml, and the influence on cell proliferation was studied. The concentration of added heparin-related substances needed to suppress the cell proliferation based on each cell growth factor by 30% is shown in Table 2.

TABLE 2

| | Concentration for Suppressing Growth Factor Dependent Cell Proliferation by 30% (µg/ml) | |
|---|---|---|
| | Cell Growth Factor | |
| Heparin-related Substance | FGF2 | VEGF165 |
| Native heparin | 248 | 520 |
| I-20 | 512 | 376 |
| N-12 | 521 | 388 |
| P-I-20 | 35 | 21 |
| P-N-12 | 41 | 29 |

As shown in FIG. 2, the polyvinylated heparin of the present invention interacts efficiently with cell growth factors in solubilized form to suppress proliferation of cells. The absorption effect with respect to this type of cell growth factor, as compared with native heparins or simple low-molecular-weight heparins, is shown to be at least 10 times as active.

As a result, the polyvinylated heparins of the present invention are shown to efficiently absorb cell growth factors or vascular growth factors derived from within the tumor tissue, so as to be capable of being used as an anti-tumor agent that effectively suppresses the growth of tumor cells and blood vessels.

Next, the proliferation of smooth muscle cells (SMC) from the human coronary artery and mesangial cells (MGC) from the human kidney cultured under the same conditions as the above paragraph aside from not adding the two types of cell growth factor was studied. The results are shown in Table 3.

TABLE 3

| | Concentration for Suppressing Growth Factor Non-dependent Cell Proliferation by 45% (µg/ml) | |
|---|---|---|
| | Cell | |
| Heparin-related Substance | FGF2 | VEGF165 |
| Native heparin | 28 | 16 |
| I-20 | 70 | 64 |
| N-12 | 80 | 70 |
| P-I-20 | 2 | 5 |
| P-N-12 | 3 | 5 |

As shown in Table 3, the proliferation of smooth muscle cells and mesangial cells which are capable of proliferation without depending on the cell growth factor in an in vitro culture are also effectively suppressed by the addition of polyvinylated heparins. This type of high proliferation suppression effect is indicated to be due to the absorption not only of cell growth factors, but also substances contained in the culture medium and cytokines created upon proliferation of the cells by means of interaction with the polyvinylated heparins. The above results suggest that the polyvinylated heparins of the present invention can not only suppress the growth of tumors, but also can be materials for preventing reconstriction after PTCA in the vicinity of the circulatory organs.

Example 9

Tumor Growth Suppressing Effect $10^6$ murine colon cancer cells Colone 26 were injected subcutaneously into the flank portions of 6–8 week old BALB/C mice. After two weeks, the formation of tumors 5 mm in diameter was confirmed, and each was given a daily subcutaneous injection in the vicinity of the tumor of 0.1 ml each of only physiological saline solution in the case of 3 examples as a control, and physiological saline solution containing the P-I-14 of the present invention (10 mg/ml) for another 3 examples. A comparison of the growth of the tumors is shown in Table 4.

TABLE 4

| Tumor Model Mice | Condition of Tumor | | |
|---|---|---|---|
| (Tumor Size 5 mm) | after 1 week | after 2 weeks | after 3 weeks |
| Control Group | Tumor Size 10–12 mm | Tumor size 20 mm or more | Tumor Size 30 mm or more |
| P-I-20-administered Group | Tumor Size 6–7 mm | Tumor Size 10 mm | Tumor Size 15 mm or less Partial tumor necrosis |

As shown in Table 4, the growth of tumors is effectively suppressed when the polyvinylated heparins of the present invention are administered. Furthermore, after 4 weeks, the control group entered a state of cancerous cachexia, extreme weight loss, paralysis of the hind legs and abnormalities in the fur were observed, and they exhibited seriously weakened conditions. In contrast, the overall condition of the group administered the polyvinylated heparins (P-I-20) of the present invention was extremely good. Additionally, in the administered group, the kidney functions and liver functions (creatinine, BUN, total bilirubin, GOT, GPT, total protein content in the blood) were no different from healthy mice, and no side effects considered to be due to polyvinylated heparin administration were observed. The above results indicate that the polyvinylated heparins of the present invention can be used as anti-tumor agents (carcinostatics) for effectively suppressing tumors due to solid cancers.

Example 10

Comparison of Interactions with Cells in Polyvinylated GAGs

A comparison of cell adhesion on dishes coated with the polyvinylated GAGs according to the above-described examples was performed. In this case, in addition to mesangial cells, human skin fibroblasts (SFB) and keratinocytes (SKC) were added for comparison. Additionally, 10 ng/ml of hrFGF-2 was added to the CECs.

The proportion (%) of adhered cells among the inoculated cells after 6 hours is shown in Table 5.

TABLE 5

| Coated Cell | P-I-20 | P-N-12 | P-I-DSA20 | P-N-20C | P-N-20D |
|---|---|---|---|---|---|
| SEB | 96 | 96 | 88 | 33 | 39 |
| SMC | 90 | 95 | 85 | 20 | 22 |
| CEC | 99 | 98 | 95 | 5 | 9 |
| SKC | 85 | 90 | 80 | 3 | 6 |

As shown in Table 5, the cell adhesion with respect to each type of functionalized glycosaminoglycan was such that the heparins exhibited high adhesion to each type of cell, but those which were N-desulfated were slightly more controlled than those which were not desulfated. On the other hand, the adhesion was strongly suppressed in chondroitin sulfate and dermatan sulfate.

In addition to the cell adhesion described above, cell culturing was performed over a period of 7 days, and the proliferation rate of the cells with respect to each functionalized glycosaminoglycan was compared. The proliferation rate was evaluated by an $OD_{540}$ value based on a cell counting reagent. Table 6 compares the proliferation rate of the cells with respect to each material.

TABLE 6

| Cell | Culture Period (days) | Cell Proliferation Rate ($OD_{450}$) on Functionalized GAG | | | | |
|---|---|---|---|---|---|---|
| | | P-I-20 | P-N-12 | P-I-DSA20 | P-N-20C | P-N-20D |
| SFB | 1 | 0.15 | 0.16 | 0.04 | 0.04 | 0.08 |
| | 2 | 0.25 | 0.30 | 0.12 | 0.12 | 0.14 |
| | 4 | 0.72 | 0.82 | 0.15 | 0.15 | 0.25 |
| | 7 | 1.50 | 1.72 | 1.63 | 0.19 | 0.41 |
| SMC | 1 | 0.14 | 0.15 | 0.14 | 0.08 | 0.10 |
| | 2 | 0.22 | 0.23 | 0.22 | 0.12 | 0.18 |
| | 4 | 0.38 | 0.39 | 0.42 | 0.20 | 0.23 |
| | 7 | 0.41 | 0.43 | 0.74 | 0.25 | 0.33 |
| CEC | 1 | 0.11 | 0.12 | 0.10 | 0.02 | 0.02 |
| | 2 | 0.18 | 0.19 | 0.17 | 0.03 | 0.04 |
| | 4 | 0.32 | 0.36 | 0.31 | 0.03 | 0.07 |
| | 7 | 0.49 | 0.50 | 0.42 | 0.02 | 0.10 |
| SKC | 1 | 0.11 | 0.13 | 0.13 | 0.09 | 0.10 |
| | 2 | 0.18 | 0.20 | 0.21 | 0.12 | 0.12 |
| | 4 | 0.31 | 0.37 | 0.38 | 0.16 | 0.28 |
| | 7 | 0.64 | 0.76 | 0.81 | 0.34 | 0.58 |

As shown in Table 6, while the proliferation rate of fibroblasts, vascular endothelial cells and skin keratinocytes in the heparin type functionalized materials was high, the proliferation rate was low in dermatan sulfate and chondroitin sulfate type functionalized materials. This difference in proliferation rate indicates a high correlation with the adhesive ability with respect to each material. On the other hand, whereas heparin is known to have a suppressing effect on the proliferation of smooth muscle cells, the heparin type functionalized materials exhibited the same level of suppression of proliferation as the dermatan sulfate and chondroitin sulfate type functionalized materials. In contrast, a reduction in the proliferation suppression effect, believed to be due to the influence of denitrified sulfuric acid, was observed in the N-desulfated heparin type functionalized materials.

From the above, it is clear that the functionalized GAGs according to the present invention reinforce the binding ability with cell proliferation factors, thus being capable of effectively controlling cell proliferation, and the control of proliferation is possible due to cell adhesion based on the carbohydrate chain structures of the GAGs themselves or the amount and position of the sulfate groups of the GAGs.

INDUSTRIAL APPLICABILITY

The functionalized materials of the present invention, being capable of performing the functions possessed by GAGs without side effects, can be used as pharmaceuticals for controlling cell proliferation, as well as being readily coated onto various types of plastic products, so as to be capable of contributing to improvements or augmenting the uses of medical materials.

What is claimed is:

1. A functionalized polymer consisting of repeating units represented by the following formula:

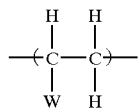

wherein, W denotes a carbohydrate chain including a structure corresponding to at least a portion of the basic skeletal structure of a glycosaminoglycan and comprising 2-50 constituent disaccharide units having an average of at least one sulfate group.

2. A functionalized polymer in accordance with claim 1, characterized in that said glycosaminoglycan is heparin, heparan sulfate, chondroitin sulfate, dermatan sulfate or a desulfated modification thereof.

3. A functionalized polymer in accordance with claim 1 wherein said functionalized polymer has a morphology in aqueous medium comprising a core composed of the polymer main chain and said carbohydrate chains W spread out from said core in said medium.

4. A functionalized polymer in accordance with claim 1, wherein said repeating units are represented by the following formula:

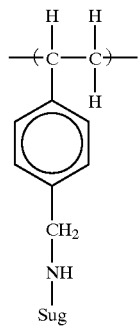

wherein Sug indicates a structure corresponding to at least a portion of the basic skeletal structure of a glycosaminoglycan and comprising 2-50 constituent disaccharide units having an average of at least one sulfate group.

5. A functionalized polymer in accordance with claim 1 comprising cell growth factors bound to said carbohydrate chains W.

6. A functionalized polymer in accordance with claim 1 comprising molecules bound to said carbohydrate chains W, said molecules being selected from the group consisting of cell growth factors, cytokines, vascular growth factors, and fibroblast growth factors.

7. A functionalized polymer in accordance with claim 3 comprising molecules bound to said carbohydrate chains W, said molecules being selected from the group consisting of cell growth factors, cytokines, vascular growth factors, and fibroblast growth factors.

8. A functionalized polymer in accordance with claim 1 wherein said carbohydrate chain W is a natural, chemically decomposed glycosaminoglycan having an aldehyde functional group that is bonded to the polymer main chain via Schiff bonding or a coupling agent.

9. A functionalized polymer in accordance with claim 1 prepared by a method comprising bonding a chemically decomposed natural glycosaminoglycan to the polymer main chain via a functional group formed by said chemical decomposition, thereby forming said carbohydrate chain W as said chemically decomposed natural glycosaminoglycan bound to the polymer main chain.

* * * * *